(12) United States Patent
Gunness (10) Patent No.: US 9,624,672 B1
(45) Date of Patent: Apr. 18, 2017

(54) SYSTEMS AND METHODS FOR LEAK DETECTION IN ROOFING AND WATERPROOFING MEMBRANES

(71) Applicant: Clark Robert Gunness, Nashville, TN (US)

(72) Inventor: Clark Robert Gunness, Nashville, TN (US)

( * ) Notice: Subject to any disclaimer, the term of this patent is extended or adjusted under 35 U.S.C. 154(b) by 0 days.

(21) Appl. No.: 15/256,766

(22) Filed: Sep. 6, 2016

Related U.S. Application Data (60) Provisional application No. 62/237,948, filed on Oct. 6, 2015.

(51) Int. Cl.
  *G01R 27/08* (2006.01)
  *E04D 13/00* (2006.01)
  *G01M 3/16* (2006.01)
  *E04G 23/02* (2006.01)

(52) U.S. Cl.
  CPC ....... *E04D 13/006* (2013.01); *E04G 23/0281* (2013.01); *G01M 3/16* (2013.01)

(58) Field of Classification Search
  CPC .... E04D 13/006; E04G 23/0281; G01M 3/16; G01N 2223/647
  USPC ...... 324/693–694, 71.1, 523, 718, 705, 557, 324/559; 702/50–51, 64–65; 52/301.1, 52/408; 73/1.17
  See application file for complete search history.

(56) References Cited

U.S. PATENT DOCUMENTS

| | | | | |
|---|---|---|---|---|
| 3,967,197 A * | 6/1976 | Anderson | ............ | G01N 27/223 324/664 |
| 4,110,945 A * | 9/1978 | Sheahan | ................. | E04D 11/02 200/61.05 |
| 4,404,516 A * | 9/1983 | Johnson, Jr. | .......... | G01M 3/045 324/525 |
| 4,543,525 A * | 9/1985 | Boryta | .................... | G01M 3/40 324/559 |
| 4,565,965 A * | 1/1986 | Geesen | ................. | E04D 13/006 324/705 |
| 4,598,273 A * | 7/1986 | Bryan, Jr. | ............. | E04D 13/006 200/61.04 |
| 4,947,470 A * | 8/1990 | Darilek | ................... | G01M 3/40 324/326 |
| 5,081,422 A * | 1/1992 | Shih | ...................... | E04D 13/006 324/693 |
| 5,184,083 A * | 2/1993 | Groover | ............... | G01N 27/205 324/357 |
| 5,288,168 A * | 2/1994 | Spencer | .................. | E02D 31/00 324/559 |
| 5,335,536 A * | 8/1994 | Runnevik | ............... | G01M 3/20 73/40.7 |
| 5,640,096 A * | 6/1997 | Alm | ....................... | G01M 3/16 324/557 |

(Continued)

*Primary Examiner* — Patrick Assouad
*Assistant Examiner* — Sean Curtis
(74) *Attorney, Agent, or Firm* — Lawson Persson + Chisholm; Catherine E. Napjus; Michael J. Persson (57) ABSTRACT

The present invention is systems and methods for detecting and locating leaks in roofing membranes and roof flashing. The systems include a conductive mesh underneath the roofing membrane and/or a conductive medium behind the roof flashing; attractor cables; and a reversible power supply attached to the conductive mesh/medium and attractor cables. The roofing membrane system also includes sensors, which may be wireless. The systems are controlled by a computer.

16 Claims, 4 Drawing Sheets

(56) References Cited

U.S. PATENT DOCUMENTS

| | | | | |
|---|---|---|---|---|
| 5,661,406 A * | 8/1997 | Daily | ............... | G01M 3/16 324/557 |
| 5,850,144 A * | 12/1998 | Howells | ............... | E02D 31/004 324/557 |
| 6,021,617 A * | 2/2000 | Sheahan | ............... | E04D 13/006 411/381 |
| 6,056,477 A * | 5/2000 | Ueda | ............... | B09B 1/00 340/605 |
| 6,167,666 B1 * | 1/2001 | Kelly | ............... | E04D 13/006 52/302.1 |
| 6,222,373 B1 * | 4/2001 | Morrison | ............... | G01M 3/16 324/532 |
| 6,331,778 B1 * | 12/2001 | Daily | ............... | G01M 3/16 324/512 |
| 7,141,982 B2 * | 11/2006 | Fink | ............... | G01M 3/40 324/444 |
| 7,142,123 B1 * | 11/2006 | Kates | ............... | G01N 27/048 340/602 |
| 7,292,155 B2 * | 11/2007 | Vokey | ............... | E04D 13/006 340/602 |
| 7,554,345 B2 * | 6/2009 | Vokey | ............... | E04D 13/006 324/522 |
| 7,652,481 B2 * | 1/2010 | Vokey | ............... | E04D 13/006 324/326 |
| 7,847,560 B2 * | 12/2010 | Vokey | ............... | E04D 13/006 324/523 |
| 7,872,479 B2 * | 1/2011 | Lorenz | ............... | G01M 3/16 324/525 |
| 8,319,508 B2 * | 11/2012 | Vokey | ............... | C23F 13/02 324/522 |
| 8,566,051 B2 * | 10/2013 | Gunness | ............... | G01M 3/16 324/444 |
| 8,970,201 B2 * | 3/2015 | Durkheim | ............... | E02D 31/004 324/71.1 |
| 9,341,540 B2 * | 5/2016 | Gunness | ............... | G01M 3/40 |
| 9,500,555 B2 * | 11/2016 | Gunness | ............... | G01M 3/16 |
| 2002/0028110 A1 * | 3/2002 | Rhee | ............... | G01M 3/04 405/129.5 |
| 2007/0024458 A1 * | 2/2007 | McGinty | ............... | G08B 21/20 340/605 |
| 2008/0143349 A1 * | 6/2008 | Lorenz | ............... | G01M 3/16 324/691 |
| 2009/0044595 A1 * | 2/2009 | Vokey | ............... | E04D 13/006 73/1.17 |
| 2009/0139178 A1 * | 6/2009 | Vokey | ............... | E04D 13/006 52/741.1 |
| 2010/0127848 A1 * | 5/2010 | Mustapha | ............... | G08B 21/20 340/505 |
| 2010/0141283 A1 * | 6/2010 | Vokey | ............... | C23F 13/02 324/705 |
| 2010/0225341 A1 * | 9/2010 | Burrows | ............... | E04D 13/006 324/718 |
| 2011/0178747 A1 * | 7/2011 | Gunness | ............... | E04D 13/006 702/65 |
| 2012/0197565 A1 * | 8/2012 | Gunness | ............... | G01M 3/16 702/64 |
| 2013/0037420 A1 * | 2/2013 | Funahashi | ............... | G01N 17/04 205/775.5 |
| 2014/0049247 A1 * | 2/2014 | Gunness | ............... | G01M 3/40 324/71.1 |
| 2014/0114590 A1 * | 4/2014 | Gunness | ............... | G01M 3/40 702/51 |
| 2014/0361796 A1 * | 12/2014 | Vokey | ............... | G01N 27/20 324/693 |
| 2015/0168329 A1 * | 6/2015 | Gunness | ............... | G01M 3/40 324/663 |
| 2015/0259923 A1 * | 9/2015 | Sleeman | ............... | E04D 11/02 52/173.1 |

* cited by examiner

SYSTEMS AND METHODS FOR LEAK DETECTION IN ROOFING AND WATERPROOFING MEMBRANES

CLAIM OF PRIORITY

This application claims the benefit of priority of U.S. Provisional Patent Application Ser. No. 62/237,948, filed on Oct. 6, 2015.

FIELD OF THE INVENTION

The present invention relates to the detection and location of water leakage in structures, and in particular to computer controlled leakage detection and location systems for roofs and roof flashing.

BACKGROUND

Roof and waterproofing membranes and linings have long been used to protect buildings, to contain water in ponds and decorative water features, to prevent leaching of contaminants from landfills, and for other purposes. While these membranes have utility, leakage through the membranes is an ongoing problem. The efforts to contain and locate leakage have resulted in the rise of specialized consultants, air and vacuum testable membranes, and, in recent history, electrical testing methods that not only determine if a leak is present in a membrane system, but where the leak is located.

Leakage in existing roofs is a particular problem, especially when the roof has a nonconductive element at the bottom of the roofing envelope next to the deck, such as a vapor barrier or a secondary roofing membrane. In these cases, water leaking into the roofing envelope can saturate the insulation and other elements in the envelope without actually leaking into the building because the lowermost membrane acts as a barrier to the water. In time, water might run into the building via penetrations, such as vent stacks, curbs for mechanical equipment, conduits, etc., through the roofing envelope and be visible from underneath. By this time, corrective action may be as extensive as cutting cores in the roofing envelope to determine the extent of water damage; removing a large portion of the roof; performing infrared or other tests to indicate the current status of the roofing envelope; etc.

Additionally, when the roofing envelope becomes saturated with water, a portion of the planned energy efficiency from the roofing envelope is lost. The building structure may also experience the corrosive effects of water, therefore compromising its penetrations. Unbeknownst to anyone, this process is occurring in thousands of roofs across North America and, indeed, in the built environment anywhere in the world.

There are methods that have been developed to address the above described problems including manual methods, such as capacitance testing, infrared scanning, and moisture probing. In addition, there are automatic systems driven by computers with sensors built into or retrofitted into the non-conductive insulation and other non-conductive materials which comprise the roofing envelope.

One known method of placing such an automatic system into a non-conductive envelope is to install relative humidity sensors in the roofing envelope, where the sensors measure humidity and temperature. An array of such sensors can give a representation of moisture conditions in a roofing envelope. Such a system is provided by Progeo GmbH of Germany and other vendors, and these systems have been used on projects in the United States. Such systems are limited in that the sensors require a certain amount of free air around them in order to determine the ambient moisture content of any part of the roofing envelope, and each sensor is only one point, measuring the relative humidity of a very small area around its location. Further, there is no guarantee that any air will circulate in the roofing envelope, and if the free flow of air is cut off, especially given the impermeable nature of closed-cell insulations in today's roofing envelopes, the sensors will not be able to sense variations in moisture, but only temperature changes.

The computer attached to such a system is given the task of correlating all the data received from the sensors in these distinct, small areas, and of producing a table, graph, or other graphic based on the extrapolations of these data. In order for the data to be at all relevant, the computer must make a correlation reading from a sensor located on the outside of the roofing envelope so that it can compare trends in relative humidity on the outside of the roof to the trends being determined by date from the sensors within the roofing envelope. The results are skewed when the temperature changes within the roofing envelope, outside the roofing envelope, or both. The skew is particularly pronounced when temperature changes precipitously, and a certain amount of time is required, sometimes days or weeks, before the system can stabilize enough to produce relevant data again. Even so, relevant data can only be surmised, as the circulation of free air in the roofing envelope cannot be adequately determined, especially across the entire expanse of the envelope. If these systems are retrofitted using tubes inserted into holes cut into the roofing envelope, the temperature sensed in the tubes is different from the actual temperature in the roofing envelope as a whole, and incorrect temperature and the contingent relative humidity measurements are inaccurate, causing false leakage alerts. Further, in order to make such a system more responsive or accurate, sensors must be deployed much closer to one another so the computer will have a greater number of points from which to draw and extrapolate data, driving the cost of the system up. In summary, such systems have significant drawbacks. In addition, the inventor has developed several automatic systems, such as those disclosed in U.S. Pat. Nos. 8,566,051 and 9,341,540 and co-pending U.S. patent application Ser. Nos. 13/442,586, 14/061,480, and 14/107,694, each of which is hereby incorporated by reference.

Another known automatic system requires a grid of hydrophobic cables, the cross-over points of which, when wetted from water flowing through the roofing membrane, make a closed circuit that identifies which portion of the grid is wet and allows location of the leakage through the membrane. This system requires water to make its way to the cross-over points to trigger an alarm and a significant flooding of a portion of the roofing envelope might occur before an alarm is tripped. Such a system is sold under the trademark DETEC.

All of the above named systems require considerable effort on the part of the contractor installing the roofing or waterproofing membrane, as the sensors must be placed within the roofing envelope as the envelope is being constructed, requiring a tremendous amount of coordination between the roofing contractor and the person or firm responsible for installing the sensors. This is because roofing on any project is subject to fits and starts because weather so drastically affects the construction schedule of the roofing envelope.

The most efficient way to build a leak detection system for membrane roofing or waterproofing, therefore, is to have the roofer install the simplest element possible of the leak detection system. In other words, if any part of the leak detection system is performed by the roofing contractor, it will be elements of the system within the roofing envelope, i.e. under the roofing or waterproofing membrane, that are elements that the roofing contractor may already customarily install. In this way, the roofing contractor will not have to deal with any more detail than is necessary to complete the roofing envelope. Thus, a conductive mesh or mat may be placed, just like a roll of roofing, underneath the membrane and within the roofing envelope. The conductive mesh or mat may be made from metal, glass, or plastic and is commonly available in various forms. This involves actions the roofer uses every day a roof is installed. This mesh may be further zoned by electrically isolating a zone or area of the mesh from other zones or areas of the mesh by simply adding a non-conductive strip of roofing or other non-conductive material. Applying strips of membrane or other sheet materials is also something a roofer does on a regular basis.

The sensors are then placed on top of the finished roofing by experienced installers of the leak detection system. This requires minimal involvement from the roofer or other trades, thus assuring that the leak detection system is properly positioned and that the membrane is not penetrated unnecessarily.

This division of labor between general roofing contractors and specialized leak detection system installers provides several advantages: The roofer does not need to be present when the sensors are installed; The sensors and wires may be installed after the roof is finished so that timing of the placement of the system can be coordinated with the last trades working on or around the roof; The sensors may be checked just before application of the overburden, if any.

Figure 1A:
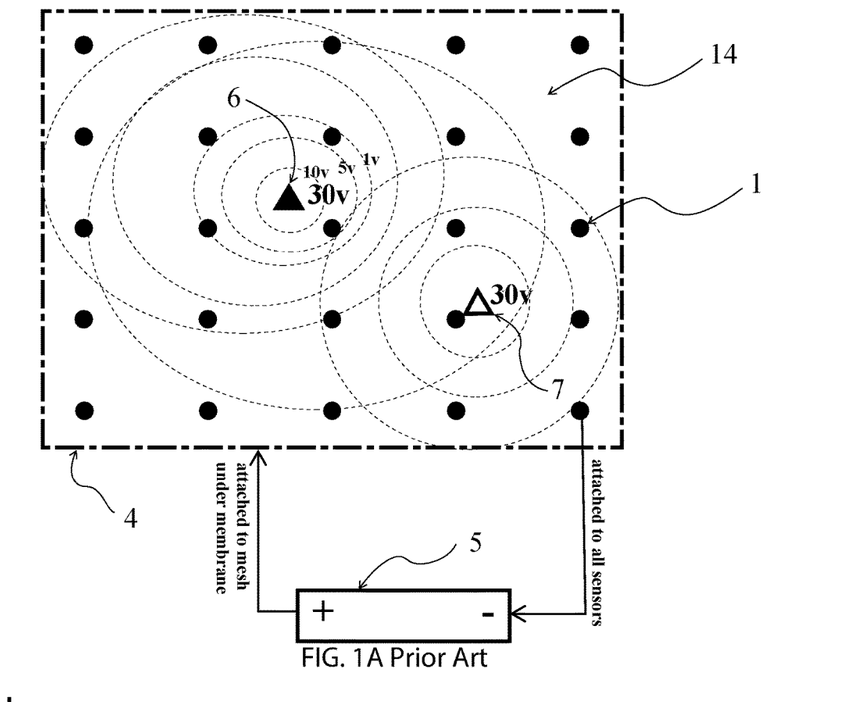
FIG. 1A is a top down diagram of a prior art leak detection system in use on a roofing membrane.
Figure 1B:
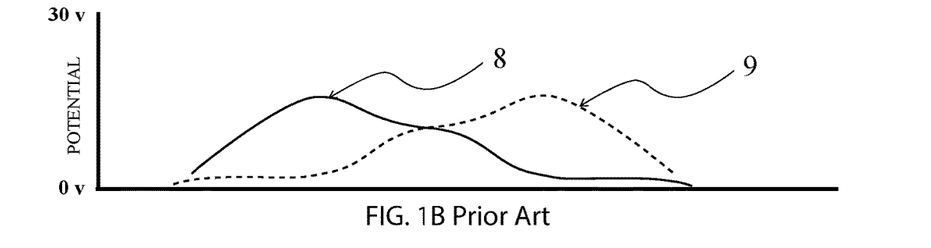
FIG. 1B is a graph of potential across one horizontal section of the membrane being tested for leaks in FIG. 1A.
Figure 1C:
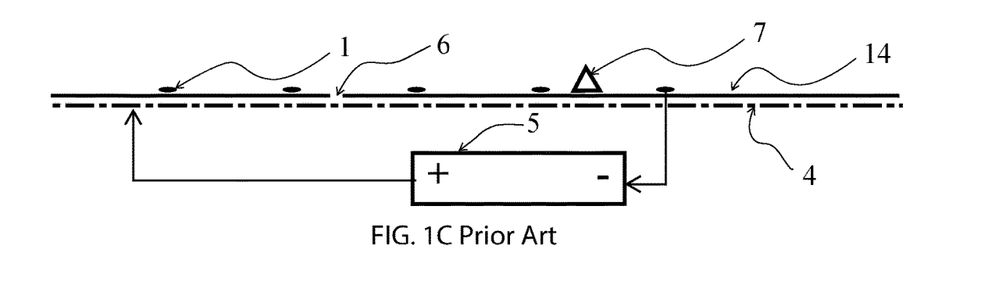
FIG. 1C is a side diagram across one horizontal section of the membrane being tested for leaks in FIG. 1A.

FIGS. 1A-1C depict a prior art system as described above. The disadvantage of placing sensors on top of the roof is accurately reading the sensors 1. The sensors 1 are placed on top of the roofing membrane 14 and surrounded by a boundary cable (not shown) placed in a loop around the sensors 1. Roofing membrane 14 is disposed on top of a conductive mesh or medium 4. The conductive mesh or medium 4 is placed under the membrane 14 and acts to attract the signal generated by a signal generator (not shown). The system also includes power supply 5. Power supply 5 references sensors 1 to the return side and powers mesh 4. As power supply 5 is common to each, if a leak 6 occurs in the membrane 14, the mesh 4 will complete the circuit and a change in the current will occur and be detected by the sensors 1. The power supply 5 for this system is contained in the computer driven module (not shown) to which the boundary cable and the sensors 1 are connected.

If all goes smoothly, as the sensors 1 and the mesh 4 are connected to the same reference, the sensor 1 that is nearest the breach 6 will read a lower voltage. The location of the breach 6 in the membrane 14 will be able to be triangulated based on the varying voltages detected by the sensors 1 disposed at different distances from the breach 6. This rarely occurs in real-world roofing or waterproofing, however, as there are elements such as stray electrical influences that contribute current to the surface of the roofing or waterproofing membrane 14, either on the bare membrane or in any type of overburden that might later be applied to the surface of the membrane 14. Examples of stray electrical influences 7 include lightning arrestor cables, conduits and vents, lighting on the roof, weather stations on the roof, power sources for devices such as lights and weather stations, anything with a power source, or anything with a transformer. It is known that these stray electrical signals 7 may compromise the discovery of leakage events or locations of leakage 6. Such stray signals 7 may be misinterpreted unless the signal from the leak detection system that generates the readings to locate an actual leak 6 is strong enough to be accurately read despite conflicting or stray signals from other, non-leak detection related elements 7, or is in some other way able to be identified as the real signal.

FIG. 1A is a top down diagram of the system with leak 6 and stray electrical influence 7. FIG. 1C is a side diagram of the same. FIG. 1B is a potential graph, showing the potential measured by various sensors 1 mapped against their location on membrane 14. The solid line 8 shows a graph of potential near actual leak 6. The dashed line 9 shows a graph of potential near stray electrical influence 7. As solid line 8 and dashed line 9 are very similar in both shape and amplitude, it would be very difficult to distinguish which is an actual leak and which is not. In other words, the signal from the leak 6 became contaminated by the stray signal 7 and, instead of lower voltage being read only at sensors 1 near the leak source 6, the voltage rises and falls in more than one area. A contour map of this situation, showing the voltage isopleth, would resemble an area with hills and valleys. FIG. 1B is a two-dimensional example, or cross section of such a map. These hills and valleys make isolating the location of the actual leak 6 extremely difficult, if not impossible.

It is possible to isolate the leak 6 manually, using an electrical balance in a process called 'vector mapping', in which two poles, one held in each hand, are connected to a balanced electrical meter so that minute changes in voltage are detected, and the needle of the meter swings toward the side that has a lower voltage. This process can easily lead a trained technician to the leak 6 as long as the technician accounts for any stray signals 7 as he or she is working the method. This is in part because the poles are held only a small distance apart, usually less than 4 feet, so compensation for stray signals 7 can be accomplished by trial and error, i.e. by moving the poles on different axes.

In an effort to eliminate the need for such manual testing, it would be possible to construct an automatic real-time leak detection that has a distance between sensors of less than 4 feet. However, it is not practical to build such tight systems in reality and further, the axis of any chain of sensors cannot be changed once the sensors are secured to the membrane.

Another element that limits the effectiveness of reading sensors 1 on top of the membrane 14 is the weather, which provides wetter and drier periods. Such weather variations may skew the readings to some extent, and because the source of the current is the boundary cable located on the perimeter of the test area, the boundary cable must be wet in order to transmit the current to the sensors in the test field. Further, any discontinuance of moisture on the surface of the membrane will affect the readings of the sensors 1 if the discontinuity of the moisture blocks the signal from the boundary cable.

It is a known fact that the overburden that covers a membrane system might allow water to flow to the membrane in some places, but not in others, resulting in an uneven distribution of water at the membrane surface. It is further known that the surface upon which the membrane system is applied can be uneven, resulting in areas of water accumulation known as ponding. Both of these conditions may change the signature of the signal generated by a boundary cable and skew the interpretation of the data acquired from manual and automatic leak location systems. If the membrane is bare, these conditions may be accommodated. After application of the overburden, however, these conditions may not be verified from the surface of the overburden that has variable areas of dry or wet and conducting or not conducting. Determining leakage from the top of the overburden or from the sensors in a system in which the boundary cable is responsible for current generation therefore becomes much more difficult.

Another problem that roofing and waterproofing systems have is that edges and penetrations account for most of the leakage in the membrane system. This is because of the amount of careful hand work required to effect the waterproofing, or flashing, of walls, vents, curbs and the like. Automatic real-time leak detection systems have struggled to determine leakage at these elements, primarily because the flashings rise and are vertical, laid against a curb, wall or stack, or the flashings are flat flanges, welded to the flat of the membrane. There was no way until the present invention of determining when and where leakage could occur in flashings.

The present invention endeavors to overcome the limitations as discussed above.

SUMMARY OF THE INVENTION

The present invention is a system for detecting and locating leaks in roofing membranes, a method for detecting and locating leaks in roofing membranes, a system for detecting and locating leaks in roof flashing, a method for detecting and locating leaks in roof flashing, a system for detecting and locating leaks in roofing membranes and roof flashing, and a method for detecting and locating leaks in roofing membranes and roof flashing.

In its most basic form, the system for detecting and locating leaks in roofing membranes includes a conductive mesh disposed under the roofing membrane to be tested; a plurality of sensors disposed on top of the roofing membrane to be tested; at least one attractor cable; a power supply attached to the mesh, the sensors, and each of the attractor cables; and a computer in electronic communication with the power supply, the mesh, the sensors, and the attractor cables.

It is preferred that the power supply power the conductive mesh and be referenced by the sensors and the attractor cables. The system also works with reverse polarity, however, with the power supply powering the sensors and the attractor cables being referenced by the conductive mesh. Discussions herein refer to the former preferred embodiment, but it is understood that the reverse is also possible. For the avoidance of doubt, as used herein, an element is "powered by" the power supply or the power supply "powers" an element if that element is attached to the positive side of the power supply. Similarly, the power supply is "referenced by" an element or an element "references" the power supply if that element is attached to the negative side of the power supply. The "positive side" and "negative side" of the power supply indicate the two poles of the power supply.

The conductive mesh or mat may be any commonly used in the art and available in various forms, such as metal, glass, or plastic meshes, conductive coatings or felts, and prefabricated conductive membranes used for manual testing purposes. The mesh may be placed directly under the roofing membrane or anywhere in the cover board or insulation layer below the membrane. The conductive mesh needs to be in a position so that it will be contacted by water if the membrane should develop a leak. In addition, the mesh cannot be touching any conductive part of the building that conducts electricity to the building or to ground. The mesh is electronically connected to the computer, which will direct the power supply to energize the mesh. As used herein, the term "conductive mesh" refers to any conductive mesh or mat as described above or commonly used in the art, such as any disclosed in the inventor's patents and co-pending patent applications, which were incorporated by reference herein.

The sensors may be any commonly used in the art, such as those disclosed in the inventor's patents and co-pending patent applications. Alternatively, the sensors may be wireless or radio frequency sensors. The wireless sensors that may be used for this purpose must reference the common (-) side of the power supply so that they can read the electrical potential from the location of the sensor to the attractor cable that also references the common side of the supply. Such wireless sensors may be used only if the power supply and the attractor cables, as well as the sensors, can all reference ground or the building in common. In such a scenario, each wireless sensor would require a single wire, which could be attached anywhere to the structure of the building, including the roof deck directly below the sensor if the deck is conductive. This would provide a common reference, as the negative side of the power supply will also be attached to the common reference, allowing voltage to be read and transmitted wirelessly by the sensor unit to the receiving unit at the computer or hub. It is understood that although such a "wireless" sensor does, in fact, include a single wire, as discussed above, it is a "wireless sensor" in that the information is transmitted wirelessly. The wireless sensors may be powered by battery, solar, microwave, or other common power sources.

The attractor cables are made from any bare or partially bare (i.e. electrical insulation is removed from a portion of, or portions of the conductor) electrical conductor made from metal wire or cable, metal or conductive polymer mesh, or other materials that conduct electricity. As used herein, the term "attractor cable" includes any of these. In addition, the attractor cables may be exposed to moisture along any or all of their length or area. Although only one attractor cable may be necessary for the system, it is preferred that several attractor cables are placed around the perimeter of the area being monitored. The attractor cables are distinct and non-attached to one another, so that each direction or leg of an attractor cable is isolated from the others. The attractor cables are essentially replacing the continuous boundary loop of prior art systems with cables that are independent of one another and not connected to one another. Each is connected to the computer, however.

The power supply energizes the mesh underneath the membrane. The sensors and the attractor cables located on the top side of the membrane, when activated by the computer, reference the other side of the power supply. As discussed throughout herein, when it is said that an element is powered or energized by the power supply, then that element is attached to the positive side of the power supply. When it is said that an element is activated, it is attached to and actively referencing the negative side of the power supply.

The power supply is preferably a low voltage unit that supplies 1-60 volts of DC power and up to 10 amps, depending on the size and construction of the membrane system. This power supply may be an AC/DC converter and transformer that is attached to any line voltage available at the location of the membrane system, or it may be powered directly by battery, solar panel, etc. The computer may be any commonly used in the art, such as those described with reference to the inventor's patent and co-pending patent applications. The computer is in electronic communication with the power supply, the mesh, the sensors, and the attractor cables. The computer includes a processor, memory, and a software product for detecting and locating leaks.

The software product is stored in the memory and is executable by the processor. The software product includes instructions for energizing the mesh, activating each of the attractor cables, recording voltage readings measured by the sensors, converting recorded voltage readings into a contour map or numerical table, and reversing the polarity of the power supply. The software product also includes the various sequencing of these instructions. As contour maps are derivatives of numerical tables and are different representations of the same data, as used herein, the term "contour map" may refer to either a contour map or a numerical table.

In some embodiments, the system also includes a moisture permeable felt or other fabric disposed on top of the sensors and attractor cables. Placing such a geotextile or other permeable, moisture retaining fabric on top of the sensors can retain moisture and provide a wider and more uniform conductive layer local to the area of moisture retention and possible leakage. As used herein, the term "felt" means any moisture permeable and/or retentive felt or fabric, such as a geotextile. Further, because the sensors reference the power supply, it is preferable, but not necessary, to have such a moisture path to the attractor cables when small areas are wet and leaking, as the sensors will still read the voltage signature from the mesh if the mesh is exposed to water via a leak in the membrane.

Figure 4A:
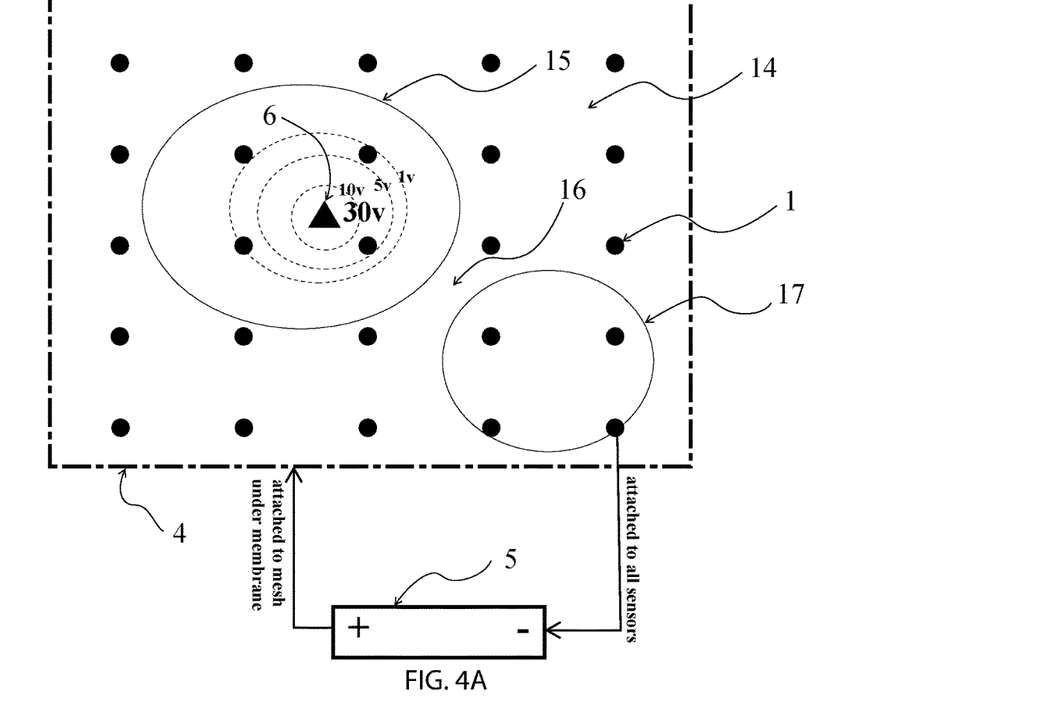
FIG. 4A is a top down diagram of a leak detection system for roofing membranes showing the effect that alternately isolated wet areas with leakage, wet areas without leakage, and dry areas have on the reading of the sensors.
Figure 4B:
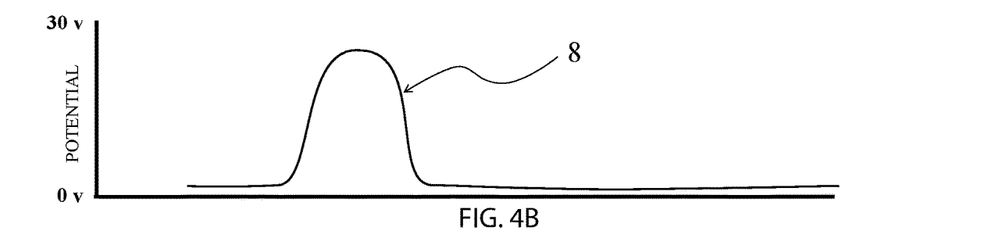
FIG. 4B is a graph of potential across one horizontal section showing the effect of the areas as shown in FIG. 4A.
Figure 4C:
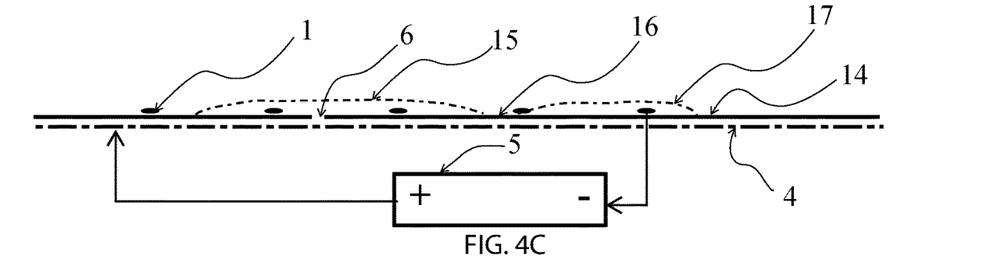
FIG. 4C is a side diagram across one horizontal section showing the effect of the areas as shown in FIG. 4A.

In operation, the mesh is first energized without the attractor cables being activated. This enables the system to overlook non-problematic wet or dry conditions on different portions of the membrane that would either confuse or render the systems of prior art useless, allowing the system to analyze only areas on the roof that are wet and leaking at the same time. The attractor cables aid in defining the location of a leak on a wider area basis, and may help eliminate stray voltage signatures from other elements in the overburden. Where a local area is wet and there is a leak, however, this will still be indicated in the leak detection system as a voltage spike emanating from the sensors close to the area of leakage and wetted in that location. FIG. 4A, 4B and 4C demonstrate this concept, and the reading generated from this initial process may be converted into a contour map or numerical table indicating high and low voltage areas, with the high voltage areas indicating the possible locations of leaks in the membrane. If the area is extensive enough, these readings may not definitely define the leak location, as other non-related elements, such as stray electrical influences in or on the roofing surface or in or on the overburden may also provide voltage signatures similar to a leak. These signatures may be large enough to blind the actual leak signal, making determination of the leak difficult, if not impossible. To mitigate this interference, one or more of the attractor cables is activated. Because the attractor cables are also referenced to the power supply, they affect the flow of current on the surface of the roofing as it relates to the electricity emanating from the leakage area. As such, they change the shape of the voltage signature from the leak, which is the other side of the reference because the leak allows water to reach the conductive mesh. The voltage signatures that are not part of the referenced circuit, i.e. the signatures created by stray electrical influences, will not change substantially with the activation of the attractor cables. Activation of the attractor cable or cables also increase the measured voltage at or near the source of the leakage, which is another clue that the leak is in that particular area. The attractor cables may be activated one at a time or all at once. Experimentation has shown that activating one attractor cable by itself, or two attractor cables disposed at an angle to one another produces good results in identifying the area and location of leakage.

In its most basic form, the method for detecting and locating leaks in a roofing membrane includes the following steps: Installing a system, which includes the steps of installing a conductive mesh underneath of a roofing membrane; connecting the conductive mesh to a power supply such that the power supply powers the conductive mesh; installing sensors on top of the roofing membrane; installing at least one attractor cable on top of the roofing membrane; connecting the attractor cables to the power supply such that they are referenced to the power supply; electronically connecting the conductive mesh, the power supply, the sensors, and each attractor cable to a computer that executes software for communicating with and/or controlling these elements; energizing the conductive mesh; polling the sensors for voltage readings for a first time; developing a voltage contour map or table from the first polling readings; activating one or more of the attractor cables; polling the sensors for voltage readings for a second time; developing a voltage contour map or table from the second polling readings; comparing the contour maps or tables from the first and second polling readings; and identifying a location of a leak from the compared first and second contour maps or tables.

The step of installing sensors may be accomplished in several different ways. In one embodiment, this step involves installing wired sensors and connecting the wired sensors to the power supply such that they are referenced to the power supply. In another embodiment, the step involves installing a wireless sensor that is referenced to ground or the common of the building and includes a single wire, and connecting that single wire to anywhere on the building. If this step of installing a wireless sensor is performed, then the additional step of referencing the power supply and the attractor cables to a common ground is also required.

In some embodiments, the steps of activating one or more of the attractor cables; polling the sensors for voltage readings for an nth time; and developing a voltage contour map or numerical table from the nth polling readings may be repeated.

In some embodiments, the method also includes the step of placing a moisture permeable felt or other fabric on top of the sensors and attractor cables.

In some embodiments, the method also includes the step of manually activating the attractor cables in order to get increased readings at a specific sensor. This step checks the validity of data received from the computer running the method. If a problem is suspected, a specific attractor with a known disposition relative to a sensor in question may be activated.

In its most basic form, the system for detecting and locating leaks in roof flashing of the present invention includes at least one segment of a conductive medium disposed behind the roof flashing to be tested; at least one attractor cable; a power supply attached to the attractor cables and the conductive medium behind the flashing; and a computer in electronic communication with the power supply, the conductive medium, and the attractor cable or cables.

The conductive medium may be any metal mesh, conductive felt, scrim, or coating. The conductive medium may be the same material as the conductive mesh discussed above with reference to the system for detecting and locating leaks in a roofing membrane of the present invention.

Although they may be the same material, "conductive mesh" is used in reference to the system for a roofing membrane and "conductive medium" is used in reference to the system for roof flashing, so as to avoid confusion as to which system is being discussed. Importantly, if this system for detecting leaks in roof flashing is used in conjunction with the system for detecting leaks in roof membranes, the conductive medium of this roof flashing system cannot touch and must be independent from and not connected to the conductive mesh of the roof membrane system. The conductive medium essentially acts as a large sensor, as discussed below, which is why additional sensors are not required for this system for detecting leaks in roof flashing, although they may be added optionally, also as discussed below. It is segmented so that when it indicates a possible leak, the leak may be localized to the position of that specific segment of conductive medium. Generally, the size of the segments is dependent on the length of the flashing to be tested and the desire to have a certain degree of resolution or localization of leakage. Several segments may be used for long portions of flashing. The more segments of conductive medium that are used, the more localized a potential leak may be. More segments require more electrical connections and a generally more cumbersome system, however. Segments should not touch, as two touching segments will act as one large segment, thus minimizing the localization advantage of having multiple segments. Designers may therefore use their best judgement in determining the size and number of conductive medium segments. The conductive medium cannot touch any conductive elements from the building or other elements not referenced to the return side of the power supply. This system for detecting leaks in roof flashing is distinct from the system for detecting leaks in roof membranes because roof flashing and roof membranes are distinct. The segmentation of the conductive medium in the system for roof flashing is also distinctive over the continuous conductive mesh used in the system for roof membranes.

The attractor cables are as described above with reference to the system for detecting and locating leaks in a roofing membrane of the present invention. The computer is also as described above with reference to the system for detecting and locating leaks in a roofing membrane of the present invention.

It is preferred that the conductive medium be referenced to the power supply and the attractor cable be powered by the power supply. The system works with the reverse polarity as well, however, with the conductive medium powered by the power supply and the attractor cable referenced to the power supply, similar to the system for roofing membranes of the present invention. Discussions herein refer to the former preferred embodiment, but it is understood that the reverse is also possible.

In some embodiments, this system also includes one or more wireless readers disposed on the conductive medium behind the flashing. The wireless reader is referenced to ground or common, so long as the power supply is referencing the same common. This is so that voltage from the live attractor cables can be detected behind the flashing by the conductive medium and the wireless reader if there is a leak. This is all that is necessary, as exact voltage measurements for triangulation are not necessary in this application, as opposed to similar applications on a roofing membrane, for example. Instead, it is only necessary that a change in voltage be detectable at the segment of the conductive medium where the leak exists.

In practice, the attractor cables are energized. A leak in the flashing may be in the body of the material of the flashing; in the welds that seal the flashing to the body of the roofing membrane; or in the sheets of flashing stuck together. If there is a leak in the flashing, the circuit between the segment of conductive medium and the power supply will complete. The completion of the circuit will be indicated in a potential spike in the contour map or numeric table readings corresponding to that segment.

In its most basic form the method for detecting and locating leaks in a roof flashing includes the following steps: Installing a system, which includes the steps of installing at least one segment of conductive medium behind the roof flashing; connecting the conductive medium to a power supply such that the segments are referenced to the power supply; installing at least one attractor cable proximate to the roof flashing; connecting the attractor cables to the power supply such that they are powered by the power supply; electronically connecting the conductive medium, the power supply, and the attractor cables to a computer that executes software for controlling these elements; energizing the attractor cables; observing a completed circuit between one of the conductive medium segments; and determining a leak location based on the location of the conductive medium segment that completed the circuit.

In some embodiments, the step of installing a system also includes the step of installing at least one wireless reader on each segment of conductive medium installed behind the flashing.

In its most basic form, the system for detecting and locating leaks in roofing membranes and roof flashing includes both the system for detecting and locating leaks in roofing membranes and the system for detecting and locating leaks in roof flashing, as described above. This combined system may be referred to herein as the "compound system." As mentioned, the conductive mesh of the roofing membrane system cannot be in contact with a segment of conductive medium of the roof flashing system. One computer may be used to control the compound system, so long as it can control all of the aspects described above with reference to either system. One power supply may be used for the compound system. It is particularly important for the polarity of that power supply to be reversible when referenced from the attractor cables or the conductive mesh. Although it is theoretically possible that only one attractor cable may be used for the entire compound system, it is preferred that several are placed near the flashing and around the roofing area to be tested.

The method for detecting and locating leaks in roofing membranes and roof flashing includes the steps listed above for both the roofing membrane method and the roof flashing method.

These aspects of the present invention are not meant to be exclusive and other features, aspects, and advantages of the present invention will be readily apparent to those of ordinary skill in the art when read in conjunction with the following description and accompanying drawings.

DETAILED DESCRIPTION

Figure 2A:
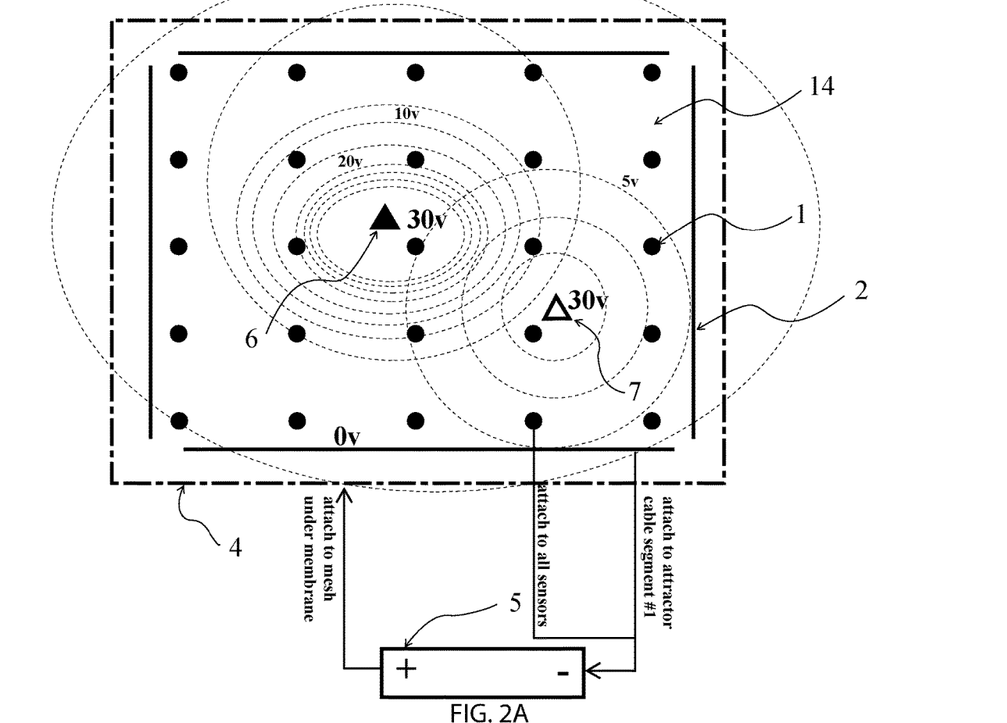
FIG. 2A is a top down diagram of a leak detection system of the present invention in use on a roofing membrane.

Referring first to FIG. 2A, a top down diagram of a leak detection system of the present invention is provided. Roofing membrane 14 is disposed on top of conductive mesh 4. An array of sensors 1 are surrounded by four non-attached attractor cables 2.

Power supply 5 powers conductive mesh 4 and is referenced by both sensors 1 and attractor cables 2. Membrane 14 has a leak 6 and a stray electrical influence 7.

When conductive mesh 4 is powered, sensors 1 provide voltage information that may be converted into a contour map that may look similar to that shown in FIG. 1B. In other words, both actual leak 6 and stray electrical influence 7 are indicating the location of possible leaks. When one or more attractor cables 2 are activated, however, the shape of the contour map changes to FIG. 2B. Leak 6 will cause water to contact conductive mesh 4. Stray electrical influence 7 will not. As attractor cables 2, sensors 1, and conductive mesh 4 are all attached to power supply 5, and stray electrical influence 7 is independent from it, activating attractor cables 2 will affect the voltages read by sensors 1 near leak 6, but not those read by sensors 1 near stray electrical influence 7. When used in conjunction with a map of the membrane 14, as shown in FIG. 2C, a comparison of the contour maps shown in FIG. 1B, created by energizing conductive mesh 4 alone, and FIG. 2B, created by energizing conductive mesh 4 and activating attractor cables 2, the location of 6 is provided and it is clear that leak 6 is the actual leak.

Figures 3A, 3B:
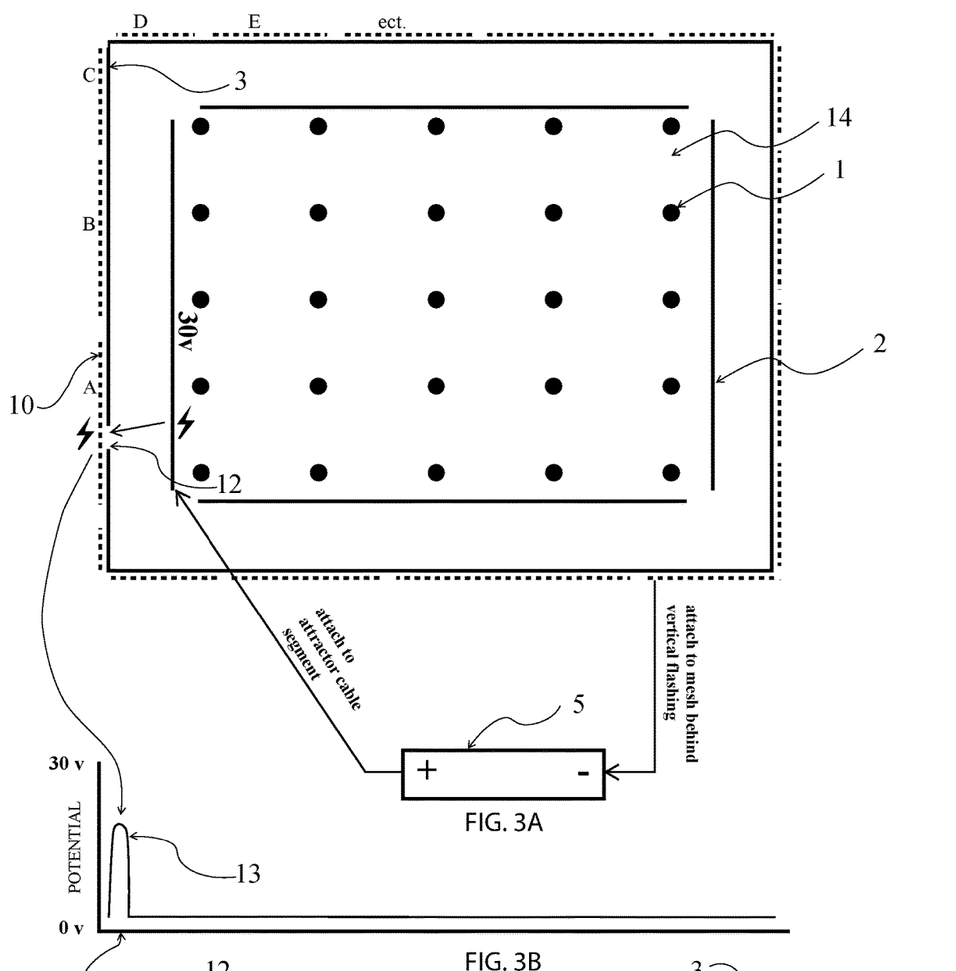
FIG. 3A is a top down diagram of a leak detection system for roofing membranes and roof flashing in use with a roofing membrane, including its flashing.
FIG. 3B is a graph of potential across one horizontal section of the membrane being tested for leaks in FIG. 3A, including its flashing.

Now referring to FIG. 3A, a top down diagram of a leak detection system for roofing membranes and roof flashing in use with a roofing membrane 14, including its flashing 3, is provided. Roofing membrane 14 is surrounded by flashing 3. The lettered segments of dotted lines around flashing 3 and membrane 14 indicate segments of conductive medium 10 behind flashing 3. Flashing 3 has a leak 12. Conductive medium 10 segment A is behind flashing 3 where leak 12 occurs.

Power supply 5 powers attractor cables 2. Conductive medium 10 segments are referenced to power supply 5. When attractor cables 2 are activated, the circuit will only be completed at conductive medium 10 segment A where leak 12 occurs. This is indicated by spike 13 in potential on the contour map shown in FIG. 3B. Spike 13 corresponds with the location of conductive medium 10 segment A, as shown in FIG. 3C, indicating the location of leak 12.

Figure 2B:
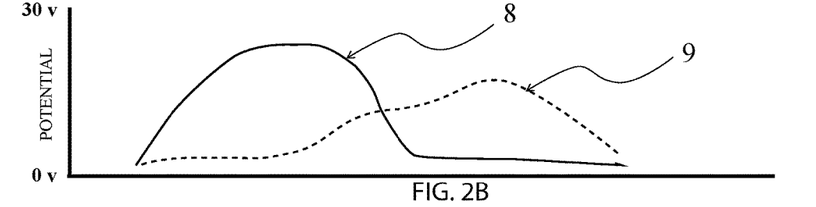
FIG. 2B is a graph of potential across one horizontal section of the membrane being tested for leaks in FIG. 2A.
Figure 2C:
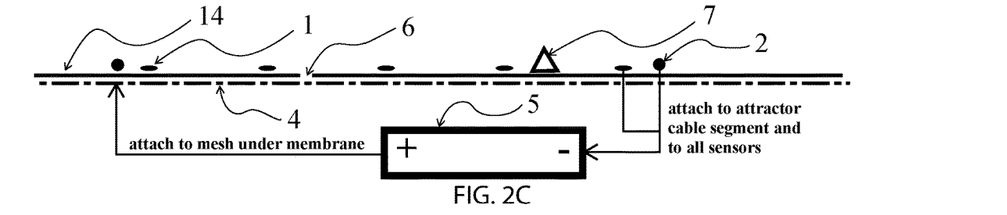
FIG. 2C is a side diagram across one horizontal section of the membrane being tested for leaks in FIG. 2A.
Figure 3C:
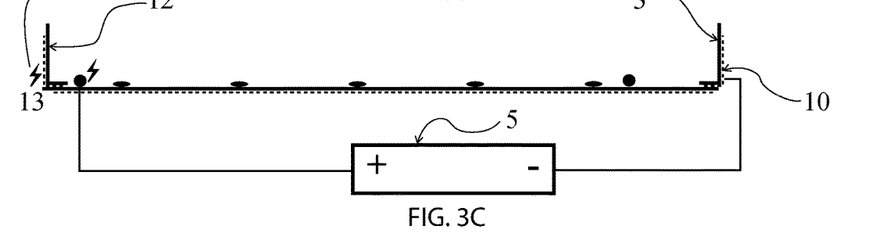
FIG. 3C is a side diagram across one horizontal section of the membrane being tested for leaks, including its flashing, in FIG. 3A.

The system described with reference to FIGS. 2A-2C is also shown in FIGS. 3A-3C. Power supply 5 is attached to each of the elements discussed with reference to those figures. By reversing the polarity of power supply 5, the elements may be alternately powered or referenced by power supply 5. One of ordinary skill in the art will recognize that the changes in the contour map that are necessary to identify the location of an actual leak may be effected with the power flowing in either direction.

Now referring to FIGS. 4A-4C, the effects on the systems for leak detection and location of the present invention of alternately isolated wet areas with leakage 15, wet areas without leakage 17, and dry areas 16 are illustrated. As shown, only wet areas with leakage 15 will cause the system to measure a potential difference. Therefore only the leak 6 will be identified by the system. Non-problematic, non-leaking wet or dry areas 17, 16 will correctly escape the systems' attention. Attractor cables 2 aid in defining the location of a leak 6 on a wider area basis, and may help eliminate stray voltage signatures from other elements in the overburden. Where a local area is wet and there is a leak 15, however, this will still be indicated in the leak detection system as a voltage spike emanating from the sensors 1 close to the area of leakage 15 and wetted in that location. The reading generated from this initial process may be converted into a contour map or numerical table indicating high and low voltage areas, such as FIG. 4B, with the high voltage areas indicating the possible locations of leaks in the membrane.

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

I claim:

1. A system for detecting and locating leaks in roof flashing of a structure, said system comprising:
    at least one segment of conductive medium disposed behind the roof flashing;
    at least one attractor cable;
    a power supply attached to said conductive medium and each of said at least one attractor cable;
    at least one wireless reader disposed on each of said segments of conductive medium behind the roof flashing, wherein said at least one wireless reader and said power supply both reference one of ground or a same common; and
    a computer in electronic communication with said power supply, said conductive medium, and each of said at least one attractor cable.

2. The system as claimed in claim 1, wherein said power supply powers each of said at least one attractor cable and is referenced by said at least one segment of conductive medium.

3. The system as claimed in claim 2, wherein said at least one segment of conductive medium is not in contact with conductive elements in said system or the structure that are referenced to said power supply.

4. The system as claimed in claim 1, wherein said power supply powers said conductive medium and is referenced by each of said at least one attractor cable.

5. The system as claimed in claim 1, wherein said at least one attractor cable is at least two attractor cables and none of said at least two attractor cables are connected.

6. The system as claimed in claim 1, wherein said at least one segment of conductive medium is at least two segments of conductive medium that do not touch.

7. A method for detecting leaks in roof flashing of a structure, said method comprising the steps of:
   installing at least one segment of conductive medium behind the roof flashing;
   connecting the at least one segment of conductive medium to a power supply such that the at least one segment of conductive medium is referenced to the power supply;
   installing at least one attractor cable;
   connecting the attractor cables to the power supply such that they are powered by the power supply;
   electronically connecting the at least one segment of conductive medium, the power supply, and the at least one attractor cable to a computer that executes software for controlling these elements;
   energizing the at least one attractor cable;
   observing a completed circuit between one of the at least one conductive medium segments; and
   determining a leak location based on the location of the at least one conductive medium segment that completed the circuit.

8. The method as claimed in claim 7, wherein said step of installing at least one segment of conductive medium comprises installing the at least one segment of conductive medium such that it is not in contact with any other installed conductive elements or the structure that are referenced to the power supply.

9. The method as claimed in claim 7, wherein said step of installing at least one attractor cable comprises installing at least two attractor cables where none of the attractor cables are in contact with one another.

10. The method as claimed in claim 7, wherein said step of installing at least one segment of conductive medium comprises installing at least two segments of conductive medium where none of the segments of conductive medium are in contact with one another.

11. The method as claimed in claim 7, further comprising the step of installing at least one wireless reader disposed on each of the at least one segment of conductive medium behind the roof flashing, wherein the at least one wireless reader and the power supply both reference one of ground or a same common.

12. A system for detecting and locating leaks in roofing membranes disposed upon a structure and roof flashing of the structure, said system comprising:
   a conductive mesh disposed under the roofing membrane and electrically isolated from any conductive part of the structure;
   a plurality of sensors disposed on top of the roofing membrane that measure voltage at a position of each of said plurality of sensors;
   at least one segment of conductive medium disposed behind the roof flashing;
   at least one attractor cable;
   a power supply attached to said conductive mesh, said plurality of sensors, said conductive medium, and each of said at least one attractor cable, wherein said at least one segment of conductive medium is not in contact with conductive elements in said system or the structure that are referenced to said power supply;
   at least one wireless reader disposed on each of said segments of conductive medium behind the roof flashing, wherein said at least one wireless reader and said power supply both reference one of ground or a same common; and
   a computer in electronic communication with said power supply, said conductive mesh, said plurality of sensors, said conductive medium, and each of said at least one attractor cable.

13. The system as claimed in claim 12, wherein said at least one attractor cable is at least two attractor cables and none of said at least two attractor cables are connected.

14. The system as claimed in claim 12, wherein said power supply powers each of said at least one attractor cable and said plurality of sensors, and is referenced by said conductive mesh and said at least one segment of conductive medium.

15. The system as claimed in claim 12, wherein said power supply powers said conductive medium and said at least one segment of conductive mesh, and is referenced by each of said at least one attractor cable and said plurality of sensors.

16. The system as claimed in claim 12, wherein said at least one segment of conductive medium is at least two segments of conductive medium that do not touch.

* * * * *